United States Patent [19]

Porter, III

[11] Patent Number: 4,840,173
[45] Date of Patent: Jun. 20, 1989

[54] ENDOTRACHEAL TUBE COMBINATION

[76] Inventor: John W. Porter, III, 6224 NE. Davis St., Portland, Oreg. 97213

[21] Appl. No.: 158,634

[22] Filed: Feb. 22, 1988

[51] Int. Cl.$^4$ ............................................. A61M 16/00
[52] U.S. Cl. ........................... 128/207.15; 128/207.14; 128/911; 128/912
[58] Field of Search .................. 128/911, 912, 205.19, 128/207.14, 205.12, 207.18, 207.15, 200.26; 604/35, 102, 128

[56] References Cited

U.S. PATENT DOCUMENTS

| 3,407,817 | 10/1968 | Galleher, Jr. | 128/207.15 |
| 4,584,998 | 4/1986 | McGrail | 128/207.15 |
| 4,607,635 | 8/1986 | Heyden | 128/207.15 |
| 4,632,108 | 12/1986 | Geil | 128/207.14 |
| 4,637,389 | 1/1987 | Heyden | 128/207.15 |
| 4,693,243 | 9/1987 | Buras | 128/207.15 |
| 4,762,125 | 8/1988 | Leiman et al. | 604/35 |

Primary Examiner—Edgar S. Burr
Assistant Examiner—Kimberly L. Asher
Attorney, Agent, or Firm—Robert L. Harrington

[57] ABSTRACT

An endotracheal tube having dual passages provided by the merging of a ventilation tube and a suction tube. The ventilation tube is adapted to project into a patient's trachea to the position of the carina anterior. An inflatable cuff surrounds the ventilation tube and prevents passage of fluids to and from the lungs. The suction passage terminates at the cuff with openings into the suction passage for suctioning secretions that pool around the cuff. The tubes as merged enable entry of the dual passages into the trachea past the vocal cords. As protruded from the patient's mouth, the tubes are separated to be connected to the respective ventilation machine and secretion suction machine.

3 Claims, 2 Drawing Sheets

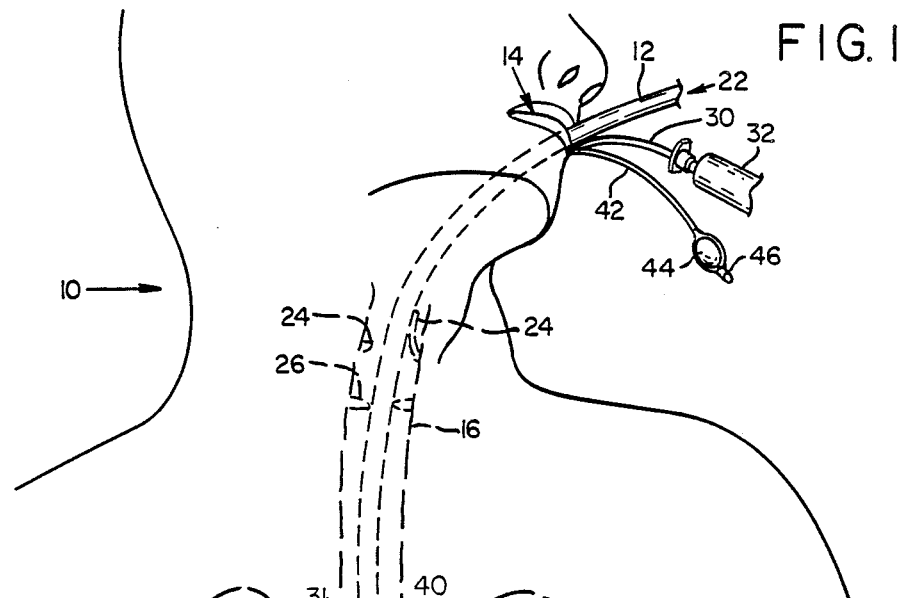
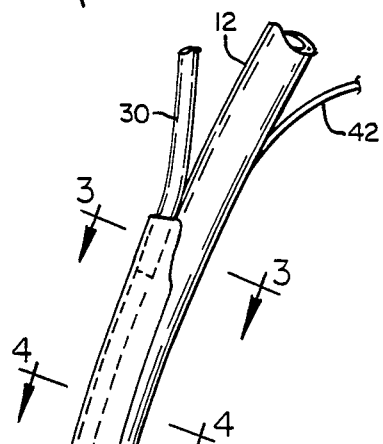
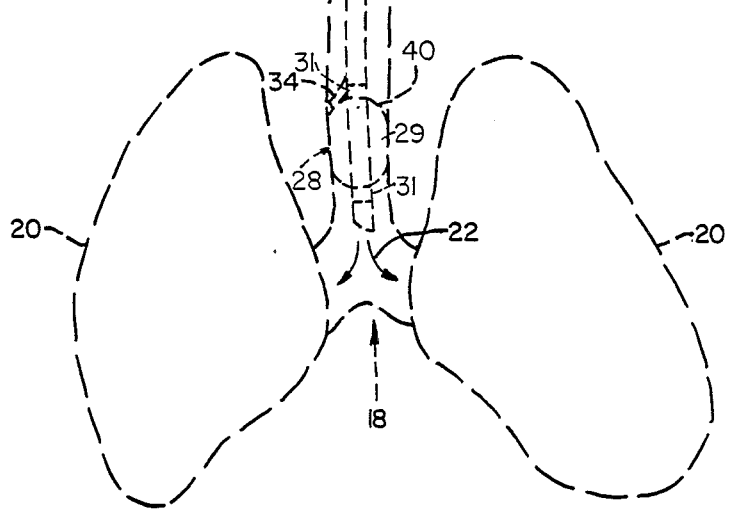
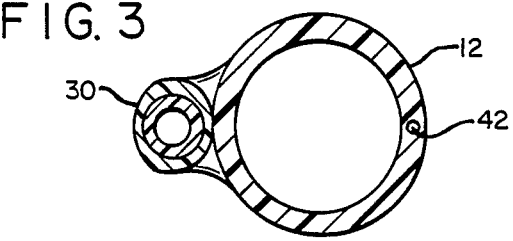
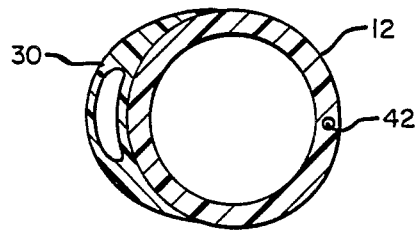
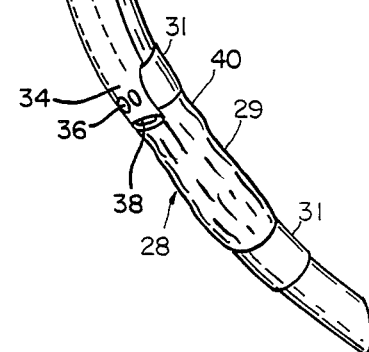

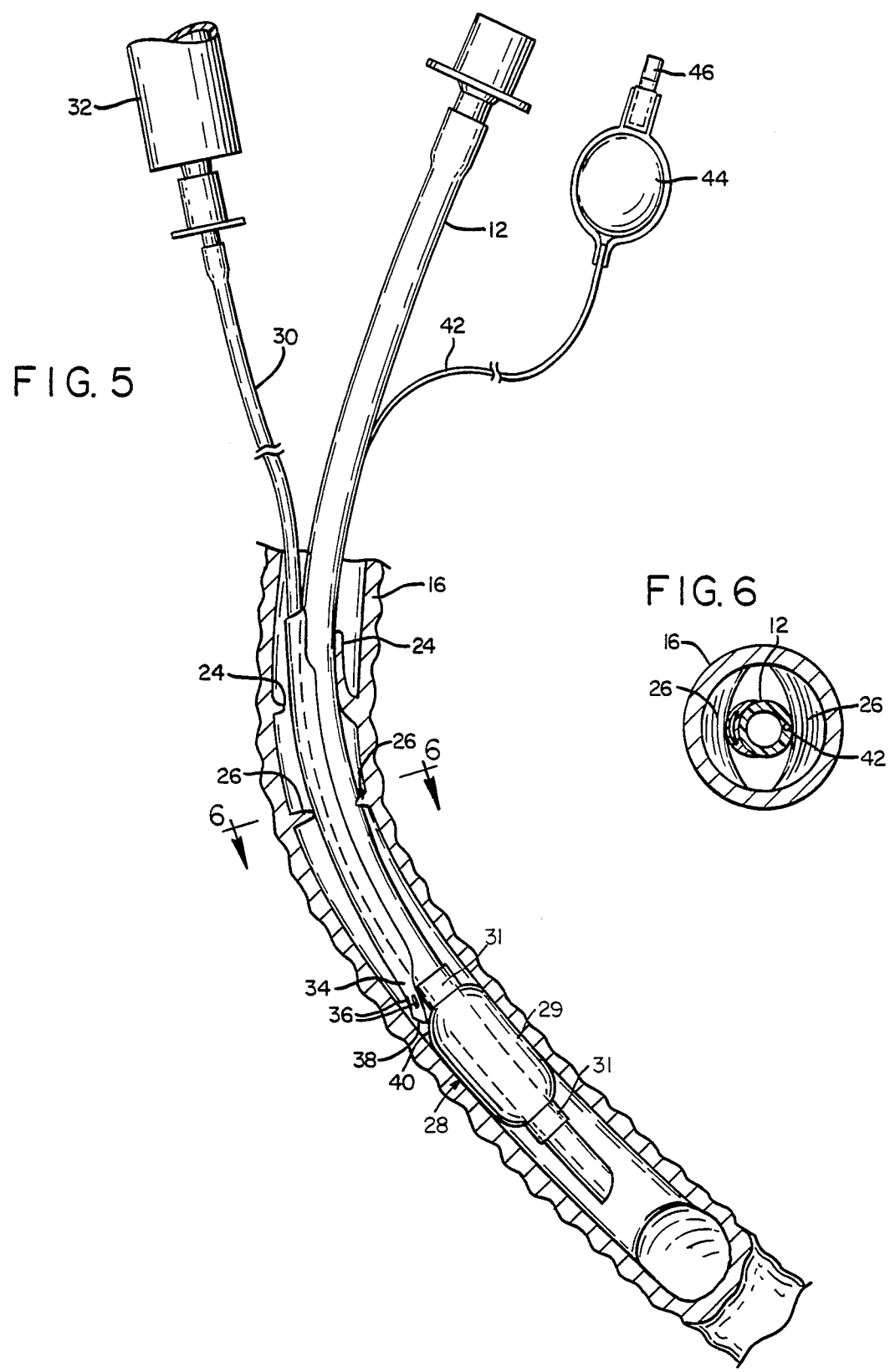

ENDOTRACHEAL TUBE COMBINATION

FIELD OF INVENTION

This invention relates to an endotracheal tube that is inserted into a hospital patient's trachea, e.g. for ventilation, and more particularly to a feature of the tube for preventing infectious fluids from entering the lungs during the process of the ventilation treatment.

BACKGROUND OF THE INVENTION

The conventional method of endotracheal intubation involves the insertion of a tubular device (an endotracheal tube) into the trachea. The endotracheal tube continues through the trachea and stops above the carina anterior to a position between the $2^{nd}$ and $4^{th}$ thoracic vertibrate, allowing the gases to be directed through the tube and into the lungs.

A primary objective of the treatment is the mechanical ventilation of the patient's lungs. This function normally induced by the patient's breathing, is typically impaired by the disease being treated. In order to create the air pressure necessary to artificially ventilate the lungs, the passageway around the tube has to be sealed. This is accomplished by an inflatable cuff provided around the tube. With the tube in place, the cuff is located about 3 to 5 centimeters above the carina and within the tube-like trachea.

The cuff is inflated to expand against the wall of the trachea and thereby to prevent gases that are being pumped into the lungs from simply backing up around the tube. This method of treatment has been quite successful for patients with chronic and acute respiratory disease. However, the method is not without complications.

Many entubated patients receiving the artificially induced ventilation may develop pneumonia. Pneumonia, which results from an infection of the lung may occur when pooled secretions, which have become infectious, are allowed, as a result of by-passing the upper airway, to enter the lungs. Unfortunately, this has been almost impossible to avoid with the prior endotracheal tubes.

The epiglottis is a form of valve that normally functions to selectively close the entry to the trachea and protect the airways (trachea and lungs) from secretions and particulate matter. The insertion of the endotracheal tube by-passes the protective system of the tracheo bronchial tree. Secretions that would normally be directed harmlessly through the digestive system follows the path of the tube, into the airway. The cuff above the carina provides a block to the downward flow of these secretions and are thus prevented from entering the lungs. The secretions become pooled above the cuff and if unattended, rapidly grow infectious bacteria that poses a serious risk to the patient.

The problem of these prior endotracheal tubes arises primarily upon cessation of the mechanical ventilation. The cuff is deflated in order to withdraw the endotracheal tube from the trachea. The infected fluid is now released to continue passage down the trachea and into the highly susceptible lungs where bronchitis or pneumonia develops rapidly. Whereas deflation of the cuff in the presence of the pooled secretions poses the greatest threat of lung infection, there is substantial risk also during treatment, i.e. with the cuff inflated. An incomplete seal caused by folds or creases in the cuff is not unusual. Whereas these folds or creases may not be a problem to the ventilation treatment it can allow microaspiration of the pooled secretions.

SUMMARY OF THE INVENTION

The preferred embodiment of the invention, in brief, provides an endotracheal tube with dual passages, i.e. a suction passage as well as a ventilation passage but separate one from the other. The suction tube is an enclosed tubular structure that is attached to or incorporated into the endotracheal tube. More accurately, it is a merging of two tubes into a unitized substantially circular configuration having dual passages. The suction passage has an inlet end opening that is located directly above a cuff surrounding the ventilation tube. Prior to deflating the cuff, and during the ventilation treatment as desired, the suction passage is used to withdraw the accumulated or pooled secretions. The endotracheal tube can be used for an extended period and removed in the prior manner without subjecting the lungs to the infectious fluids. Also, the area above the cuff can be lavaged (washed) from time to time and medications applied topically to the area above the cuff to further reduce the likelihood of infection. This is accomplished by reversing the flow through the suction tube, injecting medicated fluids into the infected area as well as withdrawing infected fluids from the area through the suction tube.

The invention will be more clearly understood by reference to the following detailed description including the accompanying drawings wherein:

FIG. 1 is a perspective view of a patient receiving ventilation treatment with an endotracheal tube of the present invention;

FIG. 2 is an enlarged view of the endotracheal tube of FIG. 1;

FIG. 3 is a sectional view as taken on view lines 3-3 of FIG. 2;

FIG. 4 is a sectional view as taken on view lines 4-4 of FIG. 2;

FIG. 5 is an enlarged view illustrating the endotracheal tube of FIG. 1 inserted into the patient's trachea which is shown in section; and FIG. 6 is a section view taken on view lines 6-6 of FIG. 5.

Reference is first made to FIG. 1 illustrating a patient 10 receiving mechanical ventilation through endotracheal intubation, herein referred to as ventilation treatment. A ventilation tube 12 extends from a source of pressurized gas (not shown) into and through the patient's mouth 14. The ventilation tube 12 continues through the trachea 16 and stops above the carina 18, allowing gases from the gas source to be directed through the tube 12 and into the lungs 20 as indicated by arrows 22.

In order for the ventilation tube 12 to be inserted into the trachea 16, it must also pass through the epiglottis 24. To accomplish this, the epiglottis 24 must be physically lifted by a laryngoscope, leaving the epiglottis 24 open so that the tube 12 may be inserted. As the tube 12 continues down the trachea 16, it has to also by-pass the vocal cords 26. The ventilation tube 12 is forced through the vocal cords 26 (see FIG. 6) and stops at its desired position above the area of the carina 18.

The epiglottis 24 normally functions to protect the airways from secretions and particulate matter. The insertion of the endotracheal tube prevents the epiglottis 24 from functioning in its normal manner.

In an attempt to provide positive pressure ventilation, a high volume low pressure cuff 28, which is attached to the ventilation tube 12 has an inflatable portion 29 and securing bands 31. The cuff is inflated 3 to 5 centimeters above the carina 18, providing a block to the back flow of gases through the trachea around the tube 12.

As explained, secretions from the patient's mouth will follow a pathway along the sides of the tube 12 but will generally be stopped by the inflated cuff 28.

This conventional method of endotracheal intubation is very familiar to experts in the field. It is also commonly known that a patient receiving the ventilation treatment is subject to the risk of pneumonia as a result of the secretions above the cuff 28 being allowed to reach the lungs 20, either during treatment if the seal around the cuff is not complete, or more likely following removal when the cuff is deflated.

Whereas removal of the secretions by a suction tube would be typically provided, that option has not heretofore been readily available. This is because of the difficulty in directing a suction tube down along the ventilation tube. Primarily the problem occurs at the vocal cord area illustrated in FIGS. 5 and 6.

The present invention provides a method of operation that largely resolves the problem of infectious fluids reaching the lungs 20 as will now be explained.

Referring now to all of the Figures, a dual passage tube combines the ventilation passage with a suction passage. The ventilation passage is provided by a continuation of the walls of tube 12, and the suction passage is provided by an exterior tube 30 connected to a suction machine or device 32 which joins the portion of the ventilation tube that enters the patient's mouth and continues into the trachea. The wall of tube 30 is merged into the tube as an appendage that continues the passageway of tube 30 along the exterior of the tube 12.

The suction tube 30, as incorporated into the endotracheal tube, causes very little or no extra impediment for inserting the tube through the passageways of the epiglottis 24 and the vocal cords 26 of the trachea 16. FIG. 3 of the drawings illustrates a sectional view of the endotracheal tube as suction tube 30 joins the ventilation tube 12 (exterior of the trachea). FIG. 4 illustrates a sectional view of the endotracheal tube with the suction tube 30 merged with the ventilation tube 12. The outer configuration is made somewhat oval shaped but generally is similar to the circular shape of the endotracheal tubes of the prior art and thus does not create any significant problem of insertion.

The termination of inserted end 34 of the tube 30 as configured and as related to the cuff 28 i.e. immediately adjacent and positioned above the cuff 28, is of particular significance. Note that four openings are provided. Three holes 36 are provided through the tube wall and the fourth is opening 38 in the end of the tube 30.

The inflatable portion 29 of cuff 28 is provided with a semi-rigid section 40 at the top of the inflatable portion of the cuff just under opening 38 of the tube 30. This is to insure that the flexible material of cuff 28 is not sucked up against the opening 38 to block it. This occurrence is also avoided by the tapered configuration of the tube end and the provision of the four openings are further insurance against total blockage as it is unlikely that all four would become blocked.

Having explained the various components of the device, its operation will now be explained.

Operation

The operation of the device is quite simple. Placement of the combination tube into the trachea for treatment of the lungs has essentially been described. The epiglottis 24 is lifted and the smooth oval-near round shaped tube is inserted down the trachea to a point just above the carina 18. The cuff 28 is inflated by pumping air into the cuff, this being accomplished through a small tube 42 that runs down inside the ventilation tube 12 and opens into the cuff interior. The air is forced down the tube 42 by use of a syringe being applied to a one-way valve 46 and into the pilot balloon 44 and thence to the cuff 28. Deflation of the cuff is accomplished simply by evacuating air from the pilot balloon 44 by using a syringe attached to the one-way valve 46.

With the trachea passage sealed, gases are pumped into the lungs and withdrawn, in effect replacing the typical breathing rhythm of the patient. It will be understood that the pressure required for expanding the lungs could not be achieved without the provision of the air seal provided by the cuff 28. The gas that is pumped into the lung can, of course, be any combination of gases with or without medication added, as prescribed by an attending physician. This function by itself is not new and not claimed as being novel to this invention.

As also described, immediately following the insertion of the endotracheal tube, secretions that normally build up in one's mouth and the bacteria that is carried by these secretions, being clinging to the tube and following the pathway past the epiglottis, into the trachea and past the vocal cords. The flow of the secretions is stopped at the cuff where it collects as an increasing pool. If unattended, the pool is an ideal incubation for the growth of infectious bacteria which are ever present in the secretions.

The novelty of the invention is in the provision of the suction passage or tube 30 merged into or integrally incorporated into the endotracheal tube. Obviously, as will be apparent from either of FIGS. 1 or 5, as soon as any pooling of the secretions take place, the holes 36,38 at the end of the suction tube are covered. Thus the tube 30 can be connected to a suction machine (32) for continuously or intermittently sucking out the secretions. With such continuous sucking action, the chance of any of the secretions leaking through the fold or creases that may have developed in the cuff is significantly reduced. In any event, it will be desireable to clear this area from time to time and particularly just prior to removal of the endotracheal tube from the patient's lungs.

An alternative is, of course, to further sterilize the area of accumulation by the cycling of a medicated solution. The solution can be inserted through the tube 30 and create its own pool around the cuff. Secretions from the mouth are then mixed into the solution where the medication serves to neutralize the bacteria. Of course, such neutralization is short lived unless there is a replenishing of the solution and thus the tube 30 is used to cycle the solution, first directing the uncontaminated solution into the area and then withdrawing the contaminated solution by a reversal of the air pressure. This same process can, of course, be used for treating other problems that may develop in the trachea, e.g. inflammation due to the presence of the endotracheal tube therein.

A number of variations will become apparent without departing from the scope of the invention. One such variation might be the provision of a second tube 30 that also terminates at the head of the cuff. One tube 30 can be used to continuously direct the medicated solution into the pooling area and the other tube 30 to continuously withdraw it.

These and other variations are considered to be encompassed by the claims appended hereto.

I claim:

1. An endotracheal tube for ventilating the lungs of a patient comprising; a ventilation tube adapted to extend from a gas source into and through the mouth of the patient, past the epiglottis into the trachea and past the vocal chords to end at a position above the carina, an inflatable cuff surrounding the tube inwardly of the extended end and when in position in the trachea, located between the carina and vocal cords, air injection means connected to the cuff for injecting air into the cuff to expand the cuff against the trachea wall for sealing off passage of air around the cuff, and a suction tube defining a suction passage, said suction tube independent of the ventilation tube at its exterior end and merging with the ventilation tube to form a near-circular configuration having independent dual passages and adaptable for passage through the epiglottis and vocal cords in the trachea, said suction passage being non-communicative with the ventilation passage, said suction tube terminating at an interior end juxtaposed to the inflated cuff to provide an open passage to the space immediately above the cuff, said suction tube end having multiple openings in communication with fluids that pool around the cuff so as not to be blocked by the cuff, said cuff has a section that is immediately adjacent to the suction tube end that is less flexible than the remainder of the inflatable cuff, said interior end of said suction tube having an end opening positioned adjacent said cuff and juxtaposed the inflated portion of said cuff whereby suction from the suction passage acting against said cuff section is inhibited from closing the openings thereof, and said suction tube having an opposite exterior end for projection out of the patient's mouth and separated from the ventilation tube, and connection means for connecting the suction tube to a source of negative air pressure.

2. A process for ventilating the lungs of a patient which comprises; providing a dual-passage endotracheal tube wherein the passages are separated at an exterior end and merged into one configuration for insertion into the trachea and past the patient's vocal cords, said dual-passage endotracheal tube inserted into the trachea of a patient, projecting one of the passage ends to the carina and terminating the second passage end short of the first passage end and past the vocal cords, sealing around the tube with an inflatable flexible cuff at a position juxtaposed to the second passage end and between the two passage ends whereby air is prevented from backing up from the lungs around the tube and secretions are prevented from passing around the sealed area into the lungs, and ventilating the patient's lungs through the one passage and suctioning substantially all the secretions that pool up due to the sealing, through the second passage end, and providing the inflatable cuff with a less flexible portion, that portion being juxtaposed the second passage end for preventing said second passage end from becoming blocked.

3. A process as defined in claim 2 wherein solutions including medication is inserted into the trachea through the second passage.

* * * * *